March 5, 1974 B. J. MACHIN ET AL Plant Pat. 3,503
CHRYSANTHEMUM PLANT
Filed May 11, 1972 3 Sheets-Sheet 1
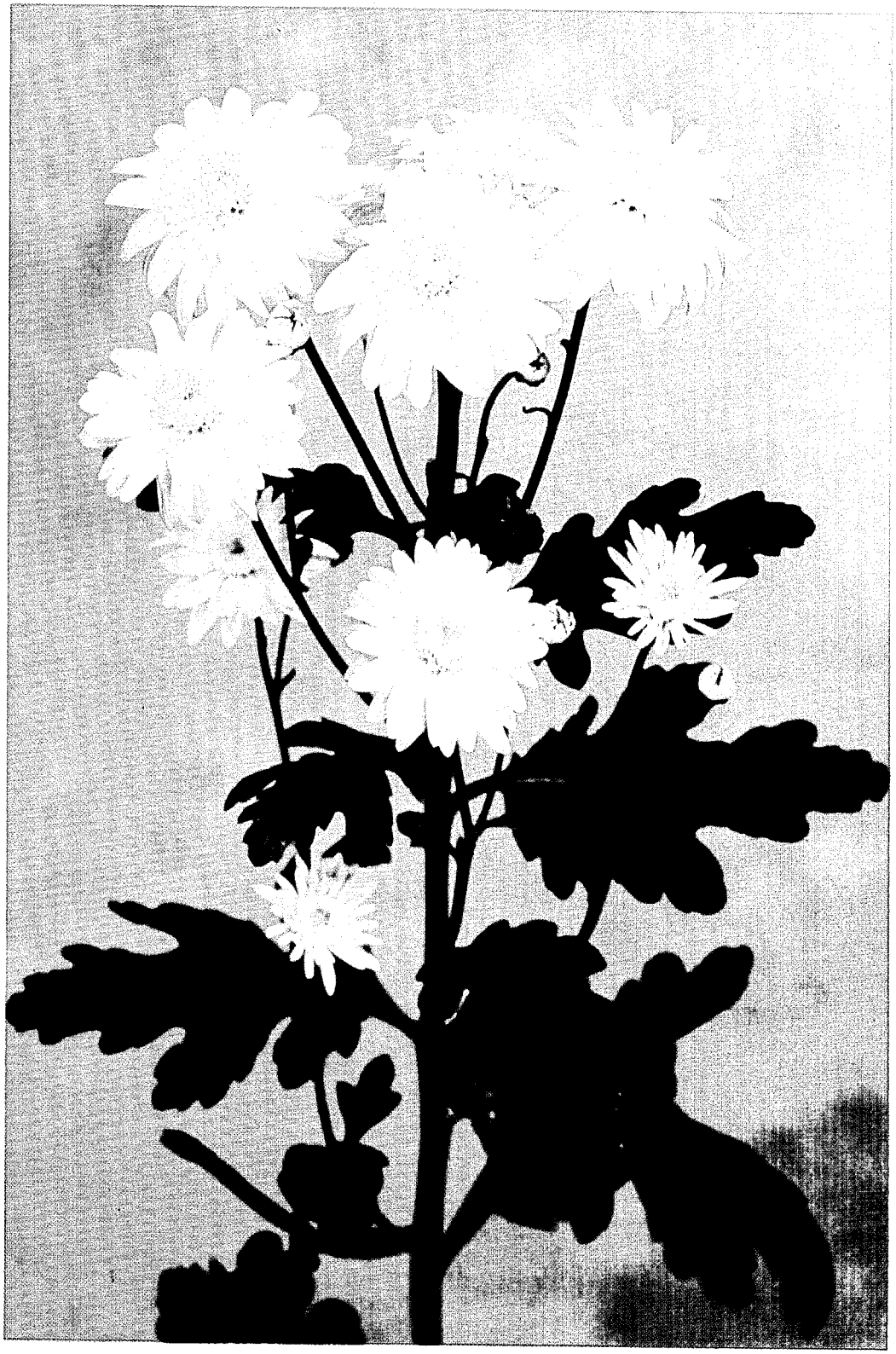

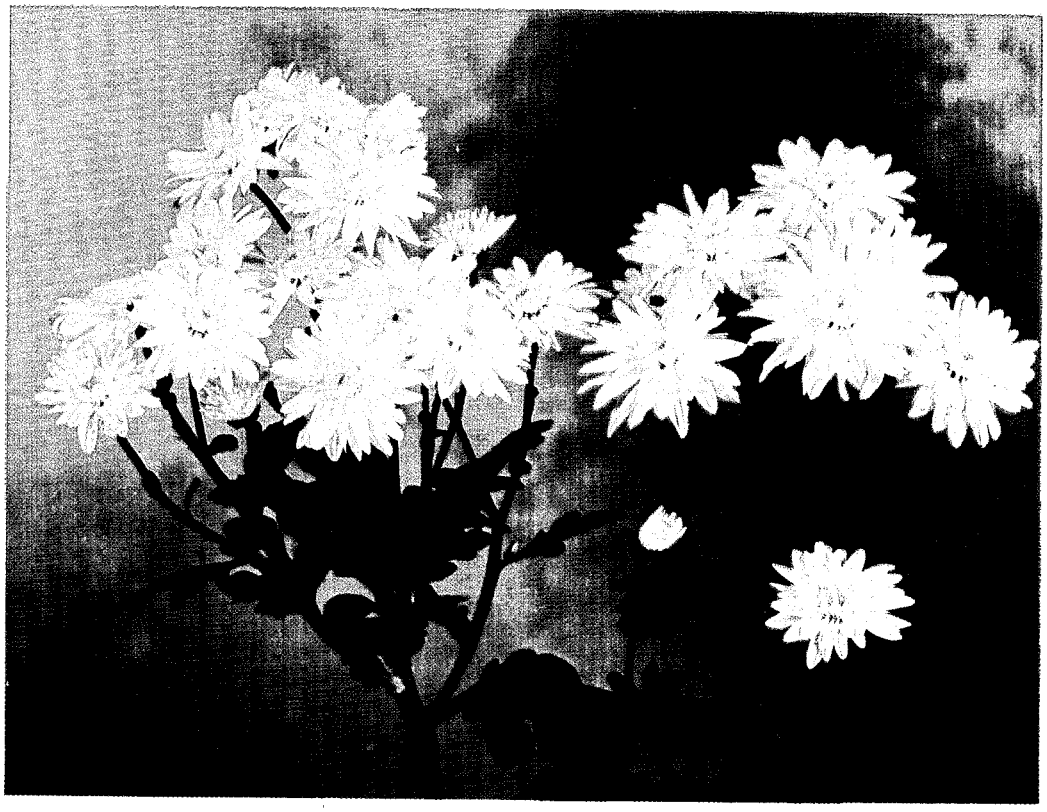

CHRYSANTHEMUM PLANT
Filed May 11, 1972
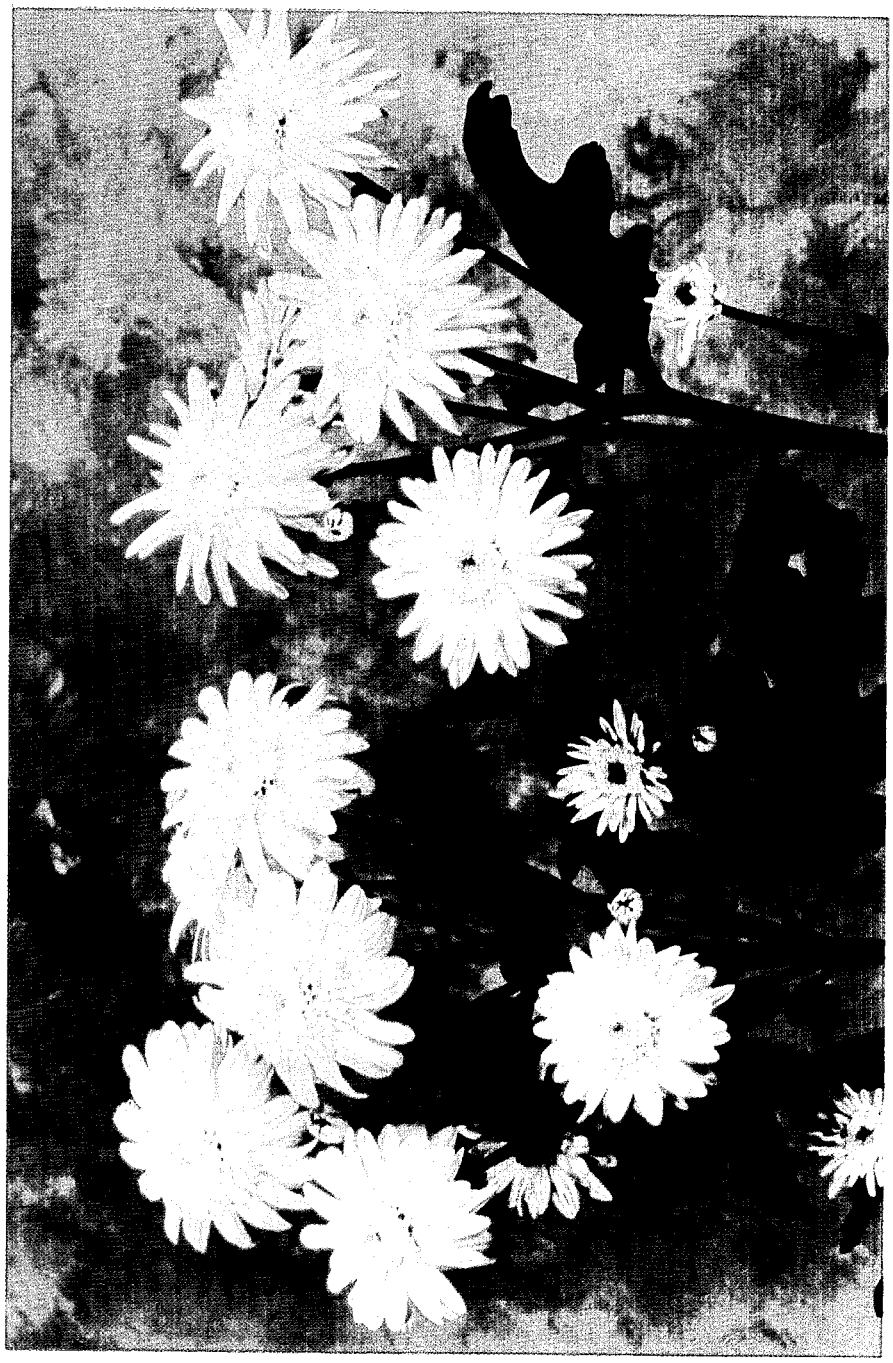

United States Patent Office

Plant Pat. 3,503

Patented Mar. 5, 1974

3,503
CHRYSANTHEMUM PLANT

Barrie J. Machin, Chichester, and Paul T. Stone, Roydon, England, assignors to Yoder Brothers, Inc., Barberton, Ohio Filed May 11, 1972, Ser. No. 252,497
Int. Cl. A01h 5/00
U.S. Cl. Plt.—74 1 Claim The present invention comprises a new and distinct cultivar of chrysanthemum plant which is a sport of the well-known, non-patented cultivar known in the United States as Yellow Sands.

The new cultivar is similar in many respects to Yellow Sands, having the same characteristics of:

(1) Foliage color, size and shape.

(2) Vigor during cool periods of year.

The new cultivar is distinguished from Yellow Sands by the following characteristics, when grown under comparable conditions:

(1) More intense golden flower color.

(2) More rounded, less pointed petals.

(3) Less longitudinal petal roll as the flowers mature.

(4) 5–7 days earlier response during high temperature periods.

(5) During the recommended period of flowering there is little or no difference in crop height. However, if the new cultivar is flowered during the high temperature period of summer when it is not recommended, there is less heat delay than in Yellow Sands, which results in less compounding of the spray formation, and 4–5″ less vigor as well as better cushion development, and a 5–7 day earlier response.

The new cultivar was discovered at Roydon, Essex, England, and was asexually reproduced by cuttings at Chichester, Sussex, England, and has been found to retain its distinctive characteristics through successive propagations.

The new cultivar when grown in the vicinity of Barberton, Ohio, has a response period of approximately 10 weeks, and the following detailed description is based on observations made of the new cultivar in a greenhouse in Barberton, Ohio. The response time, blooming period, color, and total vigor may vary significantly with varying environmental conditions such as temperature, daylength, and light intensity. Suggested flowering in the northern and western United States is from April through June, and October through mid-November; in coastal California, April through mid-November, and in the deep south, December through April.

The accompanying drawings show the unique characteristics of the new cultivar, the color being as nearly true as possible with color illustrations of this type. Sheet 1 illustrates the new cultivar itself. Sheet 2 is a comparison view showing the new cultivar on the left and the comparison cultivar Yellow Sands on the right. Sheet 3 also comprises a comparison view showing the new cultivar on the left and the comparison cultivar Yellow Sands on the right. The greater intensity of the golden yellow flower color of the new cultivar will be particularly evident, as will the less longitudinal petal roll of the new cultivar.

In the following description, color references are made to the Munsell Color Book, 1963 edition, and comparisons are made with the cultivar, Yellow Sands. Where only a single value or description appears for the new cultivar, such value or description also applies to the parent cultivar.

Botanical classification: *Chrysanthemum morifolium*

| | Golden Sands | Yellow Sands |
|---|---|---|
| Bloom: | | |
| Size | 2¼ | |
| Fully expanded | 3″ | |
| Borne | Clusters on elongated pedicels | |
| Stems | Strong | |
| Form | Anemone | |
| Permanence | 8–10 days | |
| Color | | |
| Center of flower | Golden yellow, 3.75Y8/12 | Yellow 5Y8.5/10. |
| Base of petals | Yellow, 7.5Y8.5/10 | Light yellow, 7.5Y9/6. |
| Inside of petals | do | Do. |
| Reverse of petals | Yellow, 7.5Y8.5/8 | Pale yellow, 7.5Y9/4. |
| Tonality from a distance | Golden yellow | Light yellow. |
| Discoloration | Yellow, 7.5Y8.5/8 | Pale yellow, 7.5Y9/4. |
| Petals: | | |
| Texture | Smooth | |
| Appearance and form | Open at base, broad at middle, tapering slowly to a point. | Open at base, reverse longitudinal roll tapering to a sharp point. |
| Arrangement | Composite, whorled on a single receptacle | |
| Persistence | Resist shatter | |
| Fragrance | Typical chrysanthemum | |
| Reproductive organs: | | |
| Stamen, anthers | 175–200+ | |
| Pollen | None to moderate | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Upright | |
| Height | Approximately 36″–40″ during the recommended flowering period when given 2–4 long day weeks, with a total crop time of 12–14 weeks as defined in the timetables of Yoder Brothers, Inc., Barberton, Ohio, for the various seasons. If flowered during nonrecommended high temperature periods, the average height will remain about the same, given the number of long day weeks and total crop time as defined above. | Approximately 36″–40″ during the recommended flowering period when given 2–4 long day weeks, with a total crop time of 12–14 weeks as defined in the timetables of Yoder Brothers, Inc., Barberton, Ohio, for the various seasons. If flowered in the nonrecommended high temperature periods of the year, the average height is approximately 42″–44″ given the number of long day weeks, and total crop time as defined above. |
| Spread | None when grown single stem to slight when grown pinched. | |
| Foliage: | | |
| Top side | Dark green, 10GY3/4 | |
| Size | 5¾″ long, 3⅛″ wide | |
| Quantity | Numerous | |
| Shape | Spatulate lobed | |
| Texture | Smooth | |
| Ribs and veins | Prominent | |
| Edge | Slightly indented | |
| Serration | Slight | |
| Underside | Light green, 7.5GY5/4 | |
| Stipules | Rudimentary | |

We claim:

1. A new and distinct cultivar of chrysanthemum characterized particularly as to uniqueness when compared with the parent cultivar, Yellow Sands, by its more intense golden flower color; more rounded, less pointed petals; less longitudinal petal roll; 5–7 days earlier response; better cushion development; and less compounding of sprays, and 4″–5″ shorter height during high temperature periods.

No references cited.

ROBERT E. BAGWILL, Primary Examiner